United States Patent [19]

Weber

[11] 4,279,596
[45] Jul. 21, 1981

[54] DENTAL HANDPIECE

[75] Inventor: Walter Weber, Lorsch, Fed. Rep. of Germany

[73] Assignee: Siemens Aktiengesellschaft, Berlin & Munich, Fed. Rep. of Germany

[21] Appl. No.: 101,576

[22] Filed: Dec. 10, 1979

[30] Foreign Application Priority Data

Dec. 22, 1978 [DE] Fed. Rep. of Germany ....... 2855719

[51] Int. Cl.³ .............................................. A61C 1/02
[52] U.S. Cl. .................................... 433/126; 433/99; 433/116; 433/131
[58] Field of Search ............... 433/131, 126, 130, 133, 433/146, 99, 116, 114

[56] References Cited

U.S. PATENT DOCUMENTS

| 866,518 | 9/1907 | Repsold | 433/161 |
|---|---|---|---|
| 2,370,632 | 3/1945 | Blair | 433/126 |
| 3,487,546 | 1/1970 | Beierlein et al. | 433/131 |
| 3,657,818 | 4/1972 | Garnier | 433/131 |
| 4,007,529 | 2/1977 | Fleer | 433/131 |

FOREIGN PATENT DOCUMENTS

| 1192365 | 5/1965 | Fed. Rep. of Germany | 433/99 |
|---|---|---|---|
| 1766056 | 7/1970 | Fed. Rep. of Germany | 433/126 |
| 2311496 | 9/1974 | Fed. Rep. of Germany | 433/126 |
| 2657324 | 6/1977 | Fed. Rep. of Germany | 433/114 |
| 2606062 | 8/1977 | Fed. Rep. of Germany | 433/126 |
| 667404 | 2/1952 | United Kingdom | 433/126 |

Primary Examiner—Gene Mancene
Assistant Examiner—John J. Wilson
Attorney, Agent, or Firm—Hill, Van Santen, Steadman, Chiara & Simpson

[57] ABSTRACT

A dental handpiece, which has a drive motor part with a drive shaft for rotation in a housing, and a grip section connected to the housing and having a head part with a socket for receiving and mounting a tool for rotation, and a drive train coupled to the drive shaft to transfer rotary motion from the motor to the socket, characterized by a sleeve surrounding the housing and being axially removeable from the housing and the grip section so that parts of the handpiece can be individually sterilized as necessary without subjecting the motor to sterilization.

11 Claims, 4 Drawing Figures

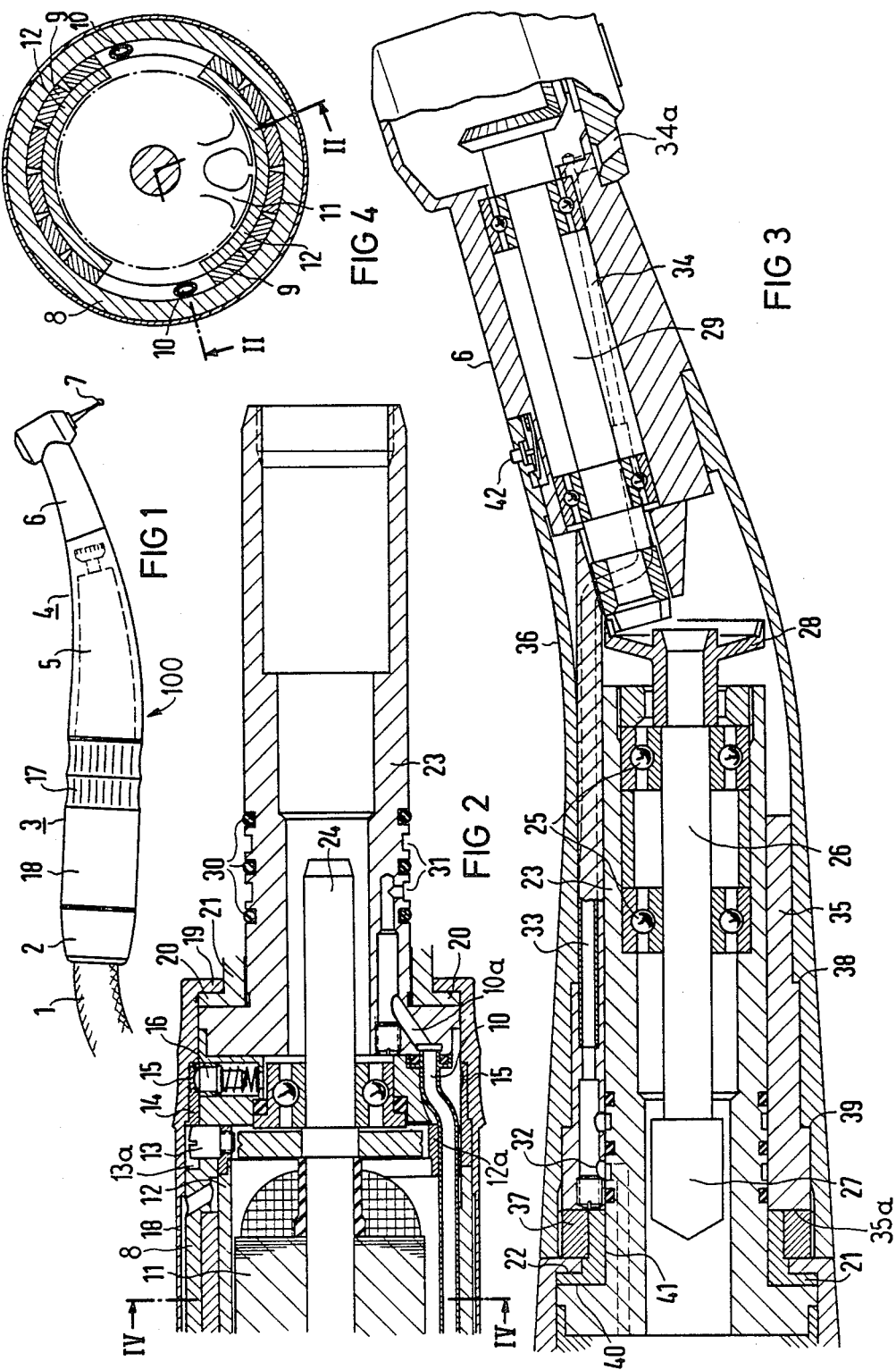

DENTAL HANDPIECE

BACKGROUND OF THE INVENTION

The present invention is directed to a dental handpiece which includes a drive motor part with a motor having a drive shaft being mounted for rotation in a housing, and a grip section, which has a head part with a socket for mounting a tool for rotation, being coupled to the housing and having a drive shaft section coupled to the drive shaft of the motor to transfer rotary motion from the motor to the socket.

In a dental practice, there exists a requirement of being able to disinfect and/or sterilize as needed the parts of the drive motor, which parts come into contact with the fingers of the dentist or technician. Since the drive motor, which is usually an electric motor, is not suited for being disinfected by being placed in a disinfecting liquid or to be sterilized by being placed in an autoclave and being subjected to superheated steam, it has been suggested to protect the motor against contact and thus against contamination by providing an extended sleeve portion on the grip section which has the head part and is coupled to the drive motor part so that the extended sleeve surrounds the motor at least over the most significant part of its length. An example of this device is disclosed in German O.S. No. 1,766,056.

A disadvantage of this type of a solution is that the grip section becomes relatively long and unwieldy. Since the sleeve-like extension is a component part of the handpiece, it must be provided for practically every handpiece. Since a sterilization or disinfection of the drive motor is not constantly required in all dental practice but rather only during specific treatments for example in surgical operations, the added expense of providing each of the grip sections with this sleeve-like extension for covering the motor is not justified.

SUMMARY OF THE INVENTION

The present invention is directed to providing a dental handpiece, which enables the portions of the drive motor part of the dental workpiece which come in contact with the hands of the physician to be disinfected and sterilized without actually requiring the grip sections to have an extended sleeve and which handpiece avoids the disadvantages of the prior art devices. The task of the invention are accomplished by an improvement in a dental handpiece having a drive motor part with a motor having a drive shaft being mounted for rotation in a housing, a grip section with a head part having a socket for receiving and mounting a tool for rotation, said grip section being coupled on the housing and having a drive shaft section coupled to the drive shaft of the motor to transfer rotary motion from the motor to the socket. The improvement comprises a sleeve surrounding the housing and means for holding the sleeve on the housing, said means allowing removal of the sleeve but preventing unintentional axial slippage from the housing of the drive motor part.

A significant advantage of this solution is that the sleeve is releasably secured on the drive motor part and in practice is usually the only sleeve and drive motor part that is present in contrast to the many different grip sections which may be employed to provide different step-down and step-up drives. By providing the sleeve, to cover the drive motor and to be contacted by the hands or fingers of the dentist or technician, the sleeve can be easily removed and disinfected or sterilized as needed and the grip section do not need to be unnecessarily extended to provide the covering sleeve as known in the prior art.

In one embodiment of the present invention, the drive motor is an electric motor which has means for controlling its operation such as changing the RPM range of the motor and the sleeve, which is rotatable on the axis of the drive motor, is coupled to the means for controlling so that rotation of the sleeve will actuate the means for controlling.

In the other preferred embodiment, the sleeve has an end adjacent the grip section which has means for releasably mounting the grip section at the said end for relative rotation to the sleeve so that both the grip section and the sleeve can be axially removed from the drive motor housing and then separated or can be separated before removal from the housing. The means for mounting includes a bushing member which is rotatably received on a guidance shank of the motor housing and has an outwardly extending flange engaging an inwardly extending flange of the sleeve. The bushing member is provided with means such as thread for threadably receiving the grip section.

BRIEF DESCRIPTION OF THE DRAWINGS

FIG. 1 is a side view of a dental handpiece in accordance with the present invention;

FIG. 2 is a longitudinal cross section of a portion of the dental handpiece of FIG. 1 taken along lines II—II of FIG. 4;

FIG. 3 is a longitudinal section of a handpiece of FIG. 1; and

FIG. 4 is a cross section taken along the lines IV—IV in FIG. 2.

DESCRIPTION OF THE PREFERRED EMBODIMENTS

The principles of the present invention are particularly useful in a dental handpiece generally indicated at 100 in FIG. 1. The handpiece 100 has a drive motor part 3 which contains an electric micro-motor and is connected to a supply hose 1 by a connector 2. The supply hose 1 provides electricity for the motor and also provides cooling fluids. The drive motor part 3 is connected to a handpiece part or grip section 4, which is composed of a first section 5 adjacent the drive motor part 3 and a head part 6 which has a socket for mounting a tool 7 for rotation. The grip section or handpiece part 4 is mounted to rotate relative to the drive motor part 3 on an axis part thereof.

As best illustrated in FIGS. 2 and 4, the drive motor part 3 has a housing 8, which receives two half-shell-shaped stator parts 9 with each part consisting of a group of members of permanent magnetic material. As illustrated in FIG. 4, the parts 9 are located in a cylindrical portion of the motor housing 8 on opposite sides of the rotor 11. In addition, the housing includes cooling lines 10, which are arranged on both sides of the cylindrical portion of the housing between the two groups of stator parts. Two return segments or adjustment members 12 are mounted in the housing 8 for rotation through an angle of at least 90° and extends between the stator parts 9 and the rotor 11 of the motor. The return segments 12 serve to influence the magnetic flux and thus influence the RPM or speed n of the motor as will be explained hereinafter.

In the position shown in FIG. 4, the return segments 12 are equal in size to the group of members forming the two magnetic half-shells 9. In this position, the air gap between the stator formed by the half-shells 9 and the rotor 11 is relatively small so that armature is permeated by the entire magnetic flux $\phi$. In the position in which the return segments 13 are turned by 90°, from the illustrated position of FIG. 4, a relatively large air gap will exist between the rotor 11 and the half-shells 9 and thus a great flux impedence is present. Moreover, a part of the magnetic flux will be short circuited by the two sections of the return segments 12. Thus, in comparison to the initial position illustrated in FIG. 4, the magnetic flux in the armature is smaller and according to the relationship $n \sim 1/\phi$, the RPM of the drive motor will be correspondingly higher. Thus by changing the position of the return segments 12 relative to the stator parts 9, the RPM range can be changed and the turning of the segments acts as a control for varying the RPM of the motor.

The actuation of the two return segments 12 occurs by a coupling pin 13, which is guided in a ring 12a which is secured to the two return segments 12. The pin 13 is guided in a slot 13a of a bushing 14. The bushing 14 has an annular groove with notches or recesses 15, which receive the ends of two spring loaded plungers 16 which are arranged in the motor housing and displaced by 180°. The guide bushing 14 is permanently connected to an outer motor jacket or first sleeve 18, which is provided with external corrugations or grooves 17 (FIG. 1) and covers the motor housing 8. When the motor jacket or sleeve 18 is rotated on the housing 8, the rotation of the coupling pin 13 will cause rotation of the segments 12.

The outer motor or jacket sleeve 18 at one end has an inwardly directed flange 19. The flange 19 covers an outwardly directed flange 20 of a bushing member or flange sleeve 21 with a minimal amount of bearing play or clearance between the surfaces 22. As illustrated, the flange sleeve or bushing member 21 is received on a guidance shank 23 of the motor housing 8, which shank surrounds a motor drive shaft 24 that extends from the motor. As illustrated in FIG. 3, the guidance shank 23 supports a drive shaft section 26 in bearings 25 and the drive section 26 on one end has a dog clutch 27 for connecting to the drive shaft 24 and on an opposite end is provided with a gear arrangement 28 having two concentric gear portions.

As best illustrated in FIG. 2, the guidance shank 23 contains two annular grooves 31, which are sealed by means of O-rings 30 and are in communication with a portion 10a of the cooling lines 10 in the drive motor part 3. As best illustrated in FIG. 3, the two annular grooves 31 are in communication with radial channels or passages 32, which are in communication with a cooling line segment 33 of a tubular part 35, which segment 33 is in communication with a segment 34 of the head part 3 which segment extends to a nozzle 34a adjacent the socket that receives the tool 7. The tubular part 35 is a sleeve-like member which is telescopically received on the guidance shank 23 and the annular grooves 31 of the shank 23 and radially extending channels 32 of the sleeve 35 form a rotatable coupling for the transfer of the cooling fluids in the lines 10 to the lines 33. The sleeve 35 is rigidly connected to an outer second sleeve or jacket 36 of the grip portion or section to rotate therewith.

On an end face 35a, the sleeve 35 lies against a threaded ring 37, which is pressed onto the flange sleeve or bushing member 21. The grip section sleeve or jacket 36 is threaded to be screwed onto the threaded ring 37. In order to position the parts in a correct axial alignment two shoulders 38 and 39 of the jacket or second sleeve 36 engaged similar shoulders on the tubular member or part 35.

The head part 6 is detachably connected to the sleeve 36 by means for operational release connection illustrated as a leaf spring lock-in mechanism 42. Thus, the head part 6 and the sleeve 36 will turn or rotate on the guidance shank 23 together with the sleeve 35, the threaded ring 37 and the flange sleeve or bushing member 21. To enable rotation of the bushing member 21 on the sleeve, clearance surfaces on an end 40 and the cylindrical inner surface 41 are provided. The bearing play or clearance provided on the end parts 19 and the bushing member 21 assures that the sleeve 18 for the motor can be turned on one hand with respect to the coupling or connector 2 and on the other hand that the head part 6 with the outer sleeve 36 of the grip portion can be turned with respect to the motor housing 8.

To remove the grip section, from the honsing 8, the head part 6 can be released by actuation of the means 42. Then the sleeve 36 and the motor sleeve 18 can be pulled off by overcoming the retaining force of the pins 16 in the recesses 15. After removal of the sleeve 36 and the sleeve 18, they can be either disconnected by unthreading the sleeve 36 from the portion 37 and then separately sterilized or they can be sterilized together. It is also possible to remove the grip section and the sleeve without removing the head part 6.

Although various minor modifications may be suggested by those versed in the art, it should be understood that I wish to embody within the scope of the patent granted hereon, all such modifications as reasonably and properly come within the scope of my contribution to the art.

I claim:

1. In a dental handpiece having a drive motor part with a motor having a drive shaft being mounted for rotation in a housing, a grip section with a head part having a socket for receiving and mounting a tool for rotation, said grip section being coupled on the housing and having a drive shaft section coupled to the drive shaft to transmit rotary motion from the motor to the socket, the improvements comprising a first sleeve surrounding said housing, means for holding the first sleeve on the housing, said means allowing removal of the sleeve but preventing unintentional axial slippage from the housing of the drive motor part and enabling rotation of the first sleeve on said housing around an axis extending parallel to the drive shaft of the drive motor part, said first sleeve having an end adjacent the grip section, said end having means for mounting the first sleeve for rotation relative to a second sleeve, said second sleeve being part of the grip section and having means forming an operational releasable connection between the head part and the second sleeve of the grip section, so that the parts can be separated without requiring assistance of tool.

2. In a dental handpiece according to claim 1, which includes means for controlling the motor in the drive motor part, a coupling element interconnecting said first sleeve to the means for controlling so that rotation of said first sleeve on the housing actuates said means for controlling.

3. In a dental handpiece according to claim 2, wherein said motor is a direct current motor having a stator formed by a permanent magnetic member, and wherein said control means comprises adjustment elements arranged between the permanent magnetic stator and the rotor of the drive motor, said adjustment elements being moveable to change the magnetic flux and therefore change the RPM of the drive motor in response to rotation of said first sleeve.

4. In a dental handpiece according to claim 1, wherein said end of the first sleeve has an inwardly extending flange, said means for mounting including a bushing member having an outwardly extending flange engaging the inwardly extending flange of the first sleeve, said grip portion being connected to said bushing member, said bushing member being rotated relative to the housing of the drive motor part so that the first sleeve, the bushing and grip member can be rotated together on the housing and the first sleeve can be rotated independent of the bushing and grip section.

5. In a dental handpiece according to claim 4, wherein the inwardly extending flange of the first sleeve and the outwardly extending flange of the bushing have sufficient clearance to enable relative rotation therebetween, said bushing member being mounted telescopically on a guidance shank of the drive motor housing with sufficient clearance between the bushing and both an end of the housing and the guidance shank to enable relative movement thereof.

6. In a dental handpiece according to claim 5, wherein the guidance shank extends beyond the drive shaft of the motor and rotatably supports a drive shaft section of the grip section, said handpiece having cooling lines extending through the drive motor part and the grip section for discharge of a cooling medium at a nozzle adjacent the socket, said cooling lines including a rotatable coupling comprising a pair of relatively moveable parts with one part having an annular groove and the other part having a passage in communication with the annular groove, said guidance shank being one of said relative moveable parts, the other part being a sleeve secured to said grip section.

7. In a dental handpiece according to claim 1, wherein said means for holding simultaneously releasably holds both the first sleeve and the grip section on the housing of the drive motor part.

8. In a dental handpiece according to claim 1, wherein said holding means comprises a detent means for selectively fixing the first sleeve in at least two distinct rotational positions on the motor housing, said detent means comprising at least one spring loaded stop pin mounted in said housing, an annular bushing received in said sleeve, said bushing having a surface concentrically arranged to the motor axis and having at least one recess disposed on said surface for receiving said stop pin.

9. In a dental handpiece having a drive motor part with a motor having a drive shaft being mounted for rotation in a housing, a grip section with a head part having a socket for receiving and mounting a tool for rotation, said grip section being coupled on the housing and having a drive shaft section coupled to the drive shaft to transmit rotary motion from the motor to the socket, the improvements comprising a first sleeve surrounding said housing, means for holding the first sleeve on the housing, said means allowing removal of the sleeve but preventing unintentional axial slippage from the housing of the drive motor part and enabling rotation of the sleeve on said housing around an axis extending parallel to the drive shaft of the drive motor part, means for controlling the motor in the drive motor part, a coupling element interconnecting said first sleeve to the means for controlling so that rotation of said sleeve on the housing actuates said means for controlling, and said holding means comprising detent means for selectively fixing the first sleeve in at least two distinct rotational positions on the motor housing, said detent means enabling axial removal of the sleeve subsequent to disengagement of the detent means.

10. In a dental handpiece according to claim 9, wherein said first sleve has an end adjacent the grip section, said end having means for mounting the first sleeve for rotation relative to a second sleeve, said second sleeve being part of the grip section and having means forming an operational releasable connection between the head part and the second sleeve of the grip section.

11. In a dental handpiece according to claim 10, wherein said end of the first sleeve has an inwardly extending flange, said means for mounting including a bushing member having an outwardly extending flange engaging the inwardly extending flange of the first sleeve, said grip section being connected to said bushing member, said bushing member being rotated relative to the housing of the drive motor part so that the first sleeve, the bushing and grip member can be rotated together on the housing and the first sleeve can be rotated independent of the bushing and grip section.

* * * * *